United States Patent
Watanabe et al.

(10) Patent No.: US 8,747,743 B2
(45) Date of Patent: Jun. 10, 2014

(54) AUTOMATIC ANALYZER

(75) Inventors: Hiroshi Watanabe, Hirachinaka (JP); Shigeki Matsubara, Hitachinaka (JP); Masanori Akutsu, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 13/515,344

(22) PCT Filed: Jan. 24, 2011

(86) PCT No.: PCT/JP2011/051252
§ 371 (c)(1),
(2), (4) Date: Jun. 27, 2012

(87) PCT Pub. No.: WO2011/093248
PCT Pub. Date: Aug. 4, 2011

(65) Prior Publication Data
US 2012/0269682 A1    Oct. 25, 2012

(30) Foreign Application Priority Data

Jan. 29, 2010 (JP) ................................ 2010-017665

(51) Int. Cl.
*G01N 21/00* (2006.01)
*G01N 35/00* (2006.01)
*G01N 33/00* (2006.01)

(52) U.S. Cl.
USPC ................................ 422/64; 436/43; 422/73

(58) Field of Classification Search
None
See application file for complete search history.

(56) References Cited

U.S. PATENT DOCUMENTS

| 4,451,433 | A | * | 5/1984 | Yamashita et al. | 422/63 |
| 5,681,530 | A | * | 10/1997 | Kuster et al. | 422/63 |
| 5,902,548 | A | * | 5/1999 | Watts et al. | 422/63 |
| 6,682,704 | B2 | * | 1/2004 | Bottwein et al. | 422/561 |
| 7,749,441 | B2 | | 7/2010 | Hanawa et al. | |
| 8,277,729 | B2 | * | 10/2012 | Matsuo et al. | 422/64 |
| 2004/0105783 | A1 | * | 6/2004 | Yamazaki et al. | 422/64 |
| 2004/0253146 | A1 | * | 12/2004 | Shiba et al. | 422/64 |
| 2005/0084426 | A1 | * | 4/2005 | Mimura et al. | 422/102 |
| 2005/0207938 | A1 | * | 9/2005 | Hanawa et al. | 422/64 |
| 2008/0003137 | A1 | * | 1/2008 | Burkhardt et al. | 422/64 |
| 2009/0035867 | A1 | * | 2/2009 | Yagi et al. | 436/50 |

FOREIGN PATENT DOCUMENTS

| JP | 2001-004637 A | 1/2001 |
| JP | 2005-037171 A | 2/2005 |
| JP | 2007-0316010 A | 6/2007 |
| JP | 2007-303879 A | 11/2007 |
| JP | 2008-203004 A | 9/2008 |
| JP | 2009-068992 A | 4/2009 |
| JP | 2009-068993 A | 4/2009 |

OTHER PUBLICATIONS

International Preliminary Report on Patentability: International Application No. PCT/JP2011/051252 dated Sep. 27, 2012.

* cited by examiner

*Primary Examiner* — Jill Warden
*Assistant Examiner* — Brittany Fisher
(74) *Attorney, Agent, or Firm* — Mattingly & Malur, PC

(57) ABSTRACT

The present invention provides an automatic analyzer including: an analyzing unit that includes an analyzing mechanism and a dispensing reagent cassette storage for storing a reagent cassette for dispensing; a reagent replenishing unit including a replenishing reagent cassette storage for storing in advance a reagent cassette for replenishing to be supplied as the reagent cassette for dispensing; and means for ejecting from the replenishing reagent cassette storage the reagent cassette for replenishing that cannot be supplied as the reagent cassette for dispensing.

11 Claims, 3 Drawing Sheets

AUTOMATIC ANALYZER

TECHNICAL FIELD

The present invention relates to automatic analyzers that analyze specimens, such as blood and urine, and more particularly to an automatic analyzer that replaces reagent cassettes.

BACKGROUND ART

Following the increase in the number of specimens to be processed and in the number of measurement items, automatic analyzers analyzing specimens, such as blood and urine, consume reagents at a more rapid pace and require that reagent cassettes be replaced at shorter intervals. Meanwhile, a need exists to reduce workloads on operators as much as possible in order to reduce personnel expenses and related cost, which necessitates simplified reagent cassette replacement procedures.

The automatic analyzers are, on the other hand, becoming able to process specimens at higher speeds, so that a need exists to minimize interruptions of analysis processes without bringing the automatic analyzer to a stop.

JP-2005-37171-A (Patent Document 1), for example, discloses an arrangement that includes, in addition to a reagent disk (dispensing reagent cassette storage) disposed in an analyzing unit, a replenishing reagent cassette storage for storing replenishing reagent cassettes for use in replacement. The arrangement further includes reagent transport means for transporting a replenishing reagent cassette from the replenishing reagent cassette storage to the reagent disk (dispensing reagent cassette storage), thereby simplifying the reagent replacement procedure and minimizing interruptions during the analysis procedure.

PRIOR ART DOCUMENTS

Patent Document

Patent Document 1
JP-2005-37171-A

SUMMARY OF THE INVENTION

Problem to be Solved by the Invention

The arrangement disclosed in Patent Document 1 includes one disposal port. A cap (cap plug) removed from the reagent cassette is discarded through the disposal port. A used reagent cassette is picked up from the reagent disk by reagent holding means and discarded through the disposal port.

Practice has it that, of the reagent cassettes existing in the reagent disk, those with expired validity dates or for purposes other than analysis that defy any analysis using the analyzing unit are conveyed onto the disposal port and discarded after screening by the operator in a manner similar to that handling used reagent cassettes. Alternatively, the automatic analysis is stopped until the operator removes the reagent cassette in question.

If the replenishing reagent cassette storage for storing the reagent cassettes for replenishment to be used for replacement does not have a refrigerating function, deterioration of reagents may need to be taken into consideration. Considering the deterioration of reagents, a need arises to intentionally discharge the reagent cassettes yet to be used from the replenishing reagent cassette storage and replaced within the day and to store these reagent cassettes in a second storage having the refrigerating function. When the reagent cassettes yet to be replaced are to be relocated to the second storage, the used reagent cassettes are also to be unloaded through the disposal port. The relocation of the reagent cassettes to the second storage is also performed by the operator who selects and picks up the relevant reagent cassette.

Furthermore, no consideration is given to handling of the reagent cassettes with expired validity dates or for purposes other than analysis that defy any analysis using the analyzing unit placed in the replenishing reagent cassette storage.

The present invention has been made in view of the foregoing problems and it is an object of the present invention to provide an automatic analyzer that minimizes interruptions of analyzing operations. The automatic analyzer does not allow any reagent shortage to occur during the analysis by ejecting replenishing reagent cassettes that are placed in a replenishing reagent cassette storage and that have expired validity dates or that cannot be supplied for analysis using an analyzing unit, and that can equip the replenishing reagent cassette storage with as many replenishing reagent cassettes to be supplied for analysis as possible.

Means for Solving the Problem

An aspect of the present invention provides an automatic analyzer including: an analyzing unit that includes an analyzing mechanism and a dispensing reagent cassette storage for storing a reagent cassette for dispensing; a reagent replenishing unit including a replenishing reagent cassette storage for storing in advance a reagent cassette for replenishing to be supplied as the reagent cassette for dispensing; and means for ejecting from the replenishing reagent cassette storage the reagent cassette for replenishing that cannot be supplied as the reagent cassette for dispensing.

Effect of the Invention

In the aspect of the present invention, the automatic analyzer includes the reagent cassette ejecting means that ejects, from the replenishing reagent cassette storage, the reagent cassette for replenishing that cannot be supplied to the analyzing unit. This allows the replenishing reagent cassette storage to store as many reagent cassettes for replenishing as possible to be supplied to the analyzing unit. This eliminates occurrence of reagent shortage during analysis and minimizes interruptions of analyzing operations.

MODES FOR CARRYING OUT THE INVENTION

Embodiments of the present invention will be described in detail below with reference to the accompanying drawings.

Figure 1:
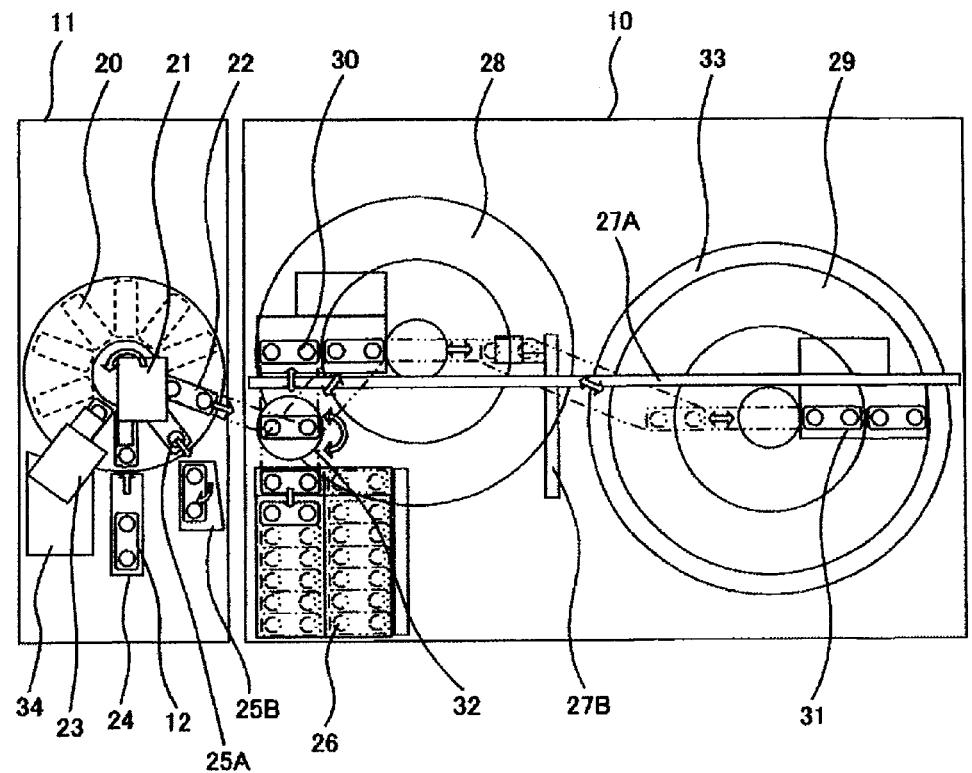
FIG. 1 is an illustration showing an outline of an automatic analyzer according to a first embodiment of the present invention.

An automatic analyzer according to a first embodiment will be described below with reference to FIGS. 1, 4(A), and 4(B).

The automatic analyzer includes an analyzing unit 10 and a reagent replenishing unit 11. The analyzing unit 10 and the reagent replenishing unit 11 are separate from each other, but may be formed integrally. In the separate configuration, the analyzing unit 10 may be used independently.

The analyzing unit 10 includes a dispensing reagent cassette storage (A) 28 and a dispensing reagent cassette storage (B) 29 for storing reagent cassettes for dispensing. The dispensing reagent cassette storage (A) 28 is disposed close to the reagent replenishing unit 11, while the dispensing reagent cassette storage (B) 29 is disposed away from the reagent replenishing unit 11. An analyzing mechanism 33 including a reaction vessel and a measuring instrument is disposed around the dispensing reagent cassette storage (B) 29.

Each of the dispensing reagent cassette storage (A) 28, the dispensing reagent cassette storage (B) 29, and the analyzing mechanism 33 is a rotatable disk. Each of the dispensing reagent cassette storage (A) 28 and the dispensing reagent cassette storage (B) 29 includes two disks disposed concentrically to form inner and outer peripheries.

A reagent cassette loading port (A) 30 is disposed on an upper side of the dispensing reagent cassette storage (A) 28. A reagent cassette loading port (B) 31 is disposed on an upper side of the dispensing reagent cassette storage (B) 29. Dispensing reagent cassettes are loaded in the disk by way of the reagent cassette loading port (A) 30 and the reagent cassette loading port (B) 31.

The analyzing unit 10 includes reagent transfer means for transferring reagent cassettes. The reagent transfer means includes a first reagent cassette transfer mechanism disposed on the side of the reagent replenishing unit, a second reagent cassette transfer mechanism disposed on the side of the reagent replenishing unit, and a reagent cassette transfer relay section disposed on the side of the reagent replenishing unit.

The second reagent cassette transfer mechanism and the reagent cassette transfer relay section will be described.

The second reagent cassette transfer mechanism includes, for example, transport guide rails 27A, 27B that constitute a transport mechanism. The analyzing unit 10 includes a reagent cassette rotating mechanism 32 disposed adjacent to the reagent cassette loading port (A) 30 of the dispensing reagent cassette storage (A) 28. The reagent cassette rotating mechanism 32 serves as the reagent cassette transfer relay section. The analyzing unit 10 further includes a discarding reagent cassette storage 26 disposed opposite to the reagent cassette loading port (A) 30 across the reagent cassette rotating mechanism 32. The reagent cassette rotating mechanism 32 changes orientation of the reagent cassette transferred from the reagent replenishing unit 11 to the reagent cassette rotating mechanism 32, so that the second reagent cassette transfer mechanism on the side of the analyzing unit can take hold of the reagent cassette easily.

The second reagent cassette transfer mechanism on the side of the analyzing unit is configured such that the transport guide rail 27A is guided along the transport guide rail 27B to move back and forth between the reagent cassette loading port (A) 30 and the discarding reagent cassette storage 26 via the reagent cassette rotating mechanism 32. In addition, the transport guide rail 28 has a length extending from the portion of the reagent cassette loading port (A) 30 of the dispensing reagent cassette storage (A) 28 to the portion of the reagent cassette loading port (B) 31 of the dispensing reagent cassette storage (B) 29.

The second reagent cassette transfer mechanism on the side of the analyzing unit conveys a reagent cassette transferred from the reagent replenishing unit 11 to the reagent cassette rotating mechanism 32 onto the reagent cassette loading port (A) 30 of the dispensing reagent cassette storage (A) 28 or the reagent cassette loading port (B) 31 of the dispensing reagent cassette storage (B) 29 and loads the reagent cassette in the disk. Additionally, the second reagent cassette transfer mechanism fetches a used reagent cassette from the dispensing reagent cassette storage (A) 28 or the dispensing reagent cassette storage (B) 29 and transfers the used reagent cassette to the discarding reagent cassette storage 26.

The reagent replenishing unit 11 includes a replenishing reagent cassette storage 20. The replenishing reagent cassette storage 20 stores in advance a replenishing reagent cassette 12 to be supplied as a dispensing reagent cassette to the dispensing reagent cassette storage (A) 28 or the dispensing reagent cassette storage (B) 29. The replenishing reagent cassette storage 20 is a rotatable disk.

The reagent replenishing unit 11 includes replenishing reagent cassette supplementary loading means 24. The replenishing reagent cassette supplementary loading means 24 has a loading port (not shown) through which the replenishing reagent cassette 12 is to be loaded. The replenishing reagent cassette 12 loaded through the loading port is loaded in the replenishing reagent cassette storage 20 by the replenishing reagent cassette supplementary loading means 24.

The reagent replenishing unit 11 includes a first reagent cassette transfer mechanism 22 included in the reagent transfer means described earlier. A replenishing reagent cassette located at the replenishing reagent cassette storage 20 is transported by the first reagent cassette transfer mechanism 22 and conveyed onto the reagent cassette rotating mechanism 32 of the reagent transfer means included in the analyzing unit 10. The reagent cassette rotating mechanism 32 is then rotated slightly to thereby change the orientation of the replenishing reagent cassette conveyed onto the reagent cassette rotating mechanism 32. Changing the orientation allows the reagent transfer means to carry the replenishing reagent cassette more easily onto the dispensing reagent cassette storage (A) 28 or the dispensing reagent cassette storage (B) 29.

The reagent replenishing unit 11 includes reagent cassette ejecting means 25A that ejects a replenishing reagent cassette located at the replenishing reagent cassette storage 20 therefrom and an ejected reagent cassette station 25B. The reagent cassette ejecting means 25A will be described in detail later.

A replenishing reagent cassette that is located at the replenishing reagent cassette storage 20, but that cannot be used for analysis should not be supplied to the dispensing reagent cassette storage (A) 28 or (B) 29. Such a replenishing reagent cassette is ejected by the reagent cassette ejecting means 25A into the ejected reagent cassette station 25B.

The reagent replenishing unit 11 includes a reagent information reading mechanism 21 that reads information on the replenishing reagent cassette located in the replenishing reagent cassette storage 20. The information on the replenishing reagent cassette read by the reagent information reading mechanism 21 is supplied to supply enable/disable determining means to be described later. It is then determined whether the replenishing reagent cassette may be supplied to the dispensing reagent cassette storage (A) 28 or (B) 29.

The replenishing reagent cassette that has been determined by the supply enable/disable determining means to be supplied to the dispensing reagent cassette storage (A) 28 or (B) 29 is to be transferred to the dispensing reagent cassette storage (A) 28 or (B) 29 by the reagent transfer means. Any replenishing reagent cassette that has been determined not to be supplied is ejected out of the replenishing reagent cassette storage 20 by the reagent cassette ejecting means 25A.

The reagent replenishing unit 11 includes cap plug opening means 23 for removing a cap plug fitted to the replenishing reagent cassette and a discarding section 34 for discarding the removed cap plug. The cap plug opening means 23 removes the cap plug from the replenishing reagent cassette placed on the replenishing reagent cassette storage 20 and the replenishing reagent cassette is then transferred to the dispensing reagent cassette storage (A) 28 or (B) 29.

The reagent cassette ejecting means 25A will be described below with reference to FIGS. 4(A) and 4(B).

Figure 4A:
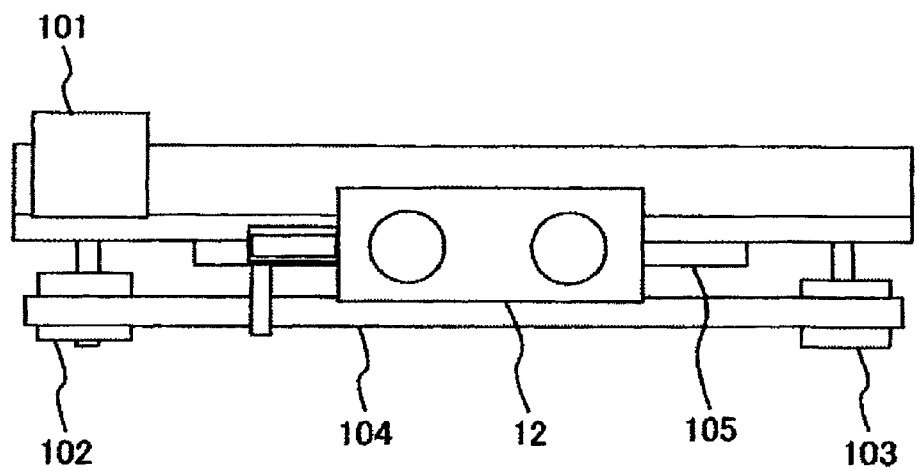
FIG. 4(A) is a plan view showing reagent cassette ejecting means included in the automatic analyzer according to the first embodiment of the present invention.
Figure 4B:
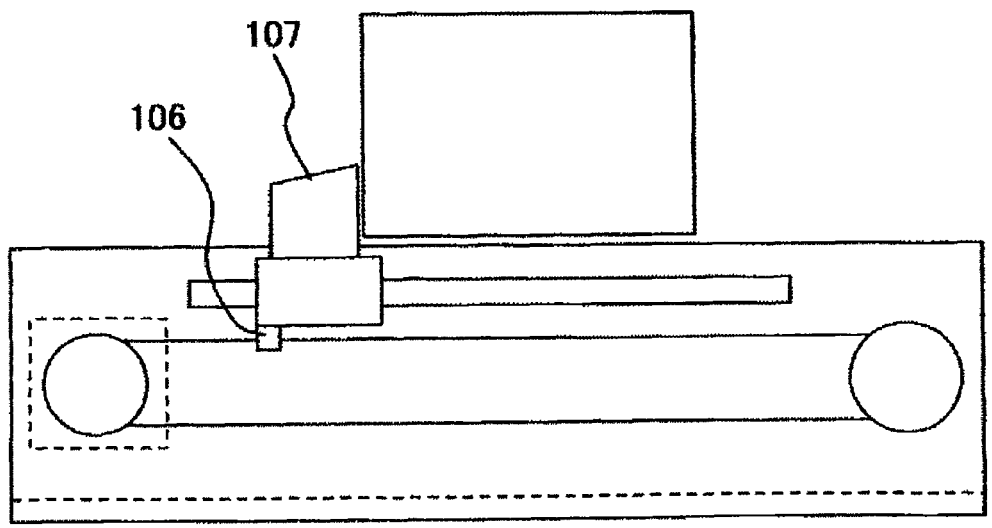
FIG. 4(B) is a front elevational view showing the reagent cassette ejecting means included in the automatic analyzer according to the first embodiment of the present invention.

FIG. 4(A) is a plan view showing the reagent cassette ejecting means. FIG. 4(B) is a front elevational view showing the reagent cassette ejecting means.

The reagent cassette ejecting means 25A is built into an inside of the reagent replenishing unit 11. The reagent cassette ejecting means 25A includes a reagent cassette pushing claw 107 for transporting the reagent cassette. The reagent cassette pushing claw 107 penetrates through a bottom surface of the replenishing reagent cassette storage 20 to thereby protrude therefrom so as to be engaged with a side surface of the reagent cassette.

The reagent cassette pushing claw 107 is connected with a connecting member 106 to a belt 104 that is driven by a cassette ejecting motor 101. The belt 104 is trained over two pulleys 103, 104 and is moved as the cassette ejecting motor 101 rotates forward or backward. This results in the reagent cassette pushing claw 107 being moved to the front and rear. The front-to-rear movement moves the replenishing reagent cassette storage 20 engaged with the reagent cassette pushing claw 107 and ejects from the replenishing reagent cassette storage 20.

Portions of a control circuit of the automatic analyzer relating to the embodiment of the present invention will be schematically described below without referring to any drawings.

The automatic analyzer performs an analysis as controlled by a computer for performing a general control. The control computer controls the analyzing unit and the reagent replenishing unit. Each of the analyzing unit and the reagent replenishing unit includes a control circuit and a control device controlled by the control computer. The control computer has the function of the supply enable/disable determining means described earlier. The operator views an operating screen and operates an operating section of the control computer to perform the analysis.

For example, the analyzing unit and the reagent replenishing unit include a power supply section, a control section, and a drive section for controlling to drive various types of devices, mechanisms, and means. Further, the supply enable/disenable detecting means in the reagent information reading mechanism 21, the reagent cassette ejecting means, the analytical measurement of the analysis unit, the reagent cassette transferring operation in the analysis unit, and the reagent cassette discarding operation in the analysis unit are controlled and operated.

Similarly, the control circuit and the control device control to load reagent cassettes into the reagent replenishing unit, transfer reagent cassettes from the reagent replenishing unit to the analyzing unit, eject those reagent cassettes that cannot be used for the analysis out of the replenishing reagent cassette storage, and to rotatably drive the replenishing reagent cassette storage and the dispensing reagent cassette storage.

Loading and transfer of the reagent cassette 12 will be described below.

When the operator loads the reagent cassette 12 into the loading port of the replenishing reagent cassette supplementary loading means 24, the reagent cassette 12 is transferred by the replenishing reagent cassette supplementary loading means 24 onto the replenishing reagent cassette storage 20.

The reagent information reading mechanism 21 of the reagent replenishing unit 11 then reads information on the reagent cassette 12 transferred onto the replenishing reagent cassette storage 20. The supply enable/disable determining means 21 then determines whether the reagent cassette 12 can be supplied as a dispensing reagent cassette to the dispensing reagent cassette storage (A) 28 or (B) 29.

Specifically, the reagent cassette 12 is affixed with an RFID tag that records such information as an amount of reagent still available for use, lot, and the validity date. The reagent information reading mechanism 21 disposed above the replenishing reagent storage 20 reads the information on the tag and stores the information in the control computer. The supply enable/disable determining means 21 of the control computer determines whether the reagent cassette 12 can be used for analysis based on the tag information, determining whether the validity date is expired or the amount of reagent still available for use is sufficient for the analysis. The reagent cassette 12 that has been determined not to be suitable for use is automatically ejected by the reagent cassette ejecting means 25A from the replenishing reagent cassette storage 20 of the reagent replenishing unit 11 to the ejected reagent cassette station 25B.

The reagent cassette 12 in the replenishing reagent cassette storage 20 is, in this manner, sequentially monitored by the supply enable/disable determining means 21 to determine whether the reagent cassette 12 can be used for analysis in the analyzing unit, so that any unnecessary reagent cassette 12 that cannot be used in the analyzing unit is not stored in the replenishing reagent cassette storage 20. As a result, the replenishing reagent cassette storage 20 can store as many replenishing reagent cassettes to be supplied to the analyzing unit as possible. This eliminates occurrence of a short supply of reagents during the analysis, minimizing interruptions of analyzing operations. It also eliminates the need for determining usability by the operator, making the analysis more efficient.

The replenishing reagent cassette determined by the supply enable/disable determining means 21 to be usable for analysis in the analyzing unit is left stored as is in the replenishing reagent cassette storage 20. When a request is received for transfer to the side of the analyzing unit 10, a corresponding replenishing reagent cassette is fed to the cap plug opening means 23 and the cap plug opening means 23 removes the cap plug from the replenishing reagent cassette. The replenishing reagent cassette from which the cap plug has been removed is conveyed as a dispensing reagent cassette by the reagent transfer means onto the dispensing reagent cassette storage (A) 28 or (B) 29 of the analyzing unit 10. The cap plug that has been removed is discarded in the discarding section 34.

Reagent replacement timing at which the replenishing reagent cassette is to be transferred from the replenishing reagent cassette storage 20 onto the dispensing reagent cassette storage (A) 28 or (B) 29 may be such an extent that a short supply of reagents does not occur. Replacement may take place using, for example, an unused cycle of a break between specimen sampling sequences or a period of time between dispensing of a first reagent and dispensing of a second reagent. If the reagent replacement is not made in time, the specimen sampling is interrupted and the reagent replacement is made after reagent dispensing for the specimen before the interruption is completed. In any case, the automatic analyzer is in the process of analyzing and is not to be temporarily stopped for replenishment of the reagent, so that time for analysis interruption can be shortened.

Transfer of the replenishing reagent cassette within the analyzing unit 10 starts where the replenishing reagent cassette is placed on the reagent cassette rotating mechanism 32 disposed in the analyzing unit 10. The reagent cassette rotating mechanism 32 rotates the replenishing reagent cassette to thereby change the orientation of the replenishing reagent cassette so that the second reagent cassette transfer mechanism can take hold of the replenishing reagent cassette easily.

The replenishing reagent cassette 12 is conveyed by the second reagent cassette transfer mechanism onto the dispensing reagent cassette storage (A) 28 or the dispensing reagent cassette storage (B) 29 according to the reagent replacement request. The second reagent cassette transfer mechanism transfers the dispensing reagent cassette that has a small amount of reagent available for use and that is to be replaced from the dispensing reagent cassette storage (A) 28 or the dispensing reagent cassette storage (B) 29 to the discarding reagent cassette storage 26. The dispensing reagent cassette is left in the discarding reagent cassette storage 26 until the operator removes the same therefrom.

A second embodiment will be described in detail below with reference to FIG. 2.

The second embodiment will be described with particular emphasis on differences from the first embodiment and descriptions of similarities which are denoted similar reference numerals will be omitted.

An automatic analyzer includes an analyzing unit 10 and a reagent replenishing unit 11. The analyzing unit 10 of the second embodiment is characterized in that a reagent cassette discharge storage 43 is disposed adjacent to a discarding reagent cassette storage 26. The analyzing unit 10 of the second embodiment is otherwise similarly arranged as the analyzing unit 10 of the first embodiment shown in FIG. 1.

A reagent cassette 12 for dispensing located at a dispensing reagent cassette storage (A) 28 or a dispensing reagent cassette storage (B) 29 may temporarily need to be stored in another reagent storage. The operator intentionally issues a command to meet such a need from, for example, an operating screen. On receipt of the command, a second reagent cassette transfer mechanism of reagent transfer means fetches the corresponding reagent cassette 12 from the dispensing reagent cassette storage (A) 28 or the dispensing reagent cassette storage (B) 29 and transfers the reagent cassette 12 onto the reagent cassette discharge storage 43. A used reagent cassette 12 is stored in the discarding reagent cassette storage 26, while a reagent cassette 12 yet to be used or still available for use is separately stored in the reagent cassette discharge storage 43. This separate storage facilitates subsequent handling of the reagent cassette 12.

Figure 2:
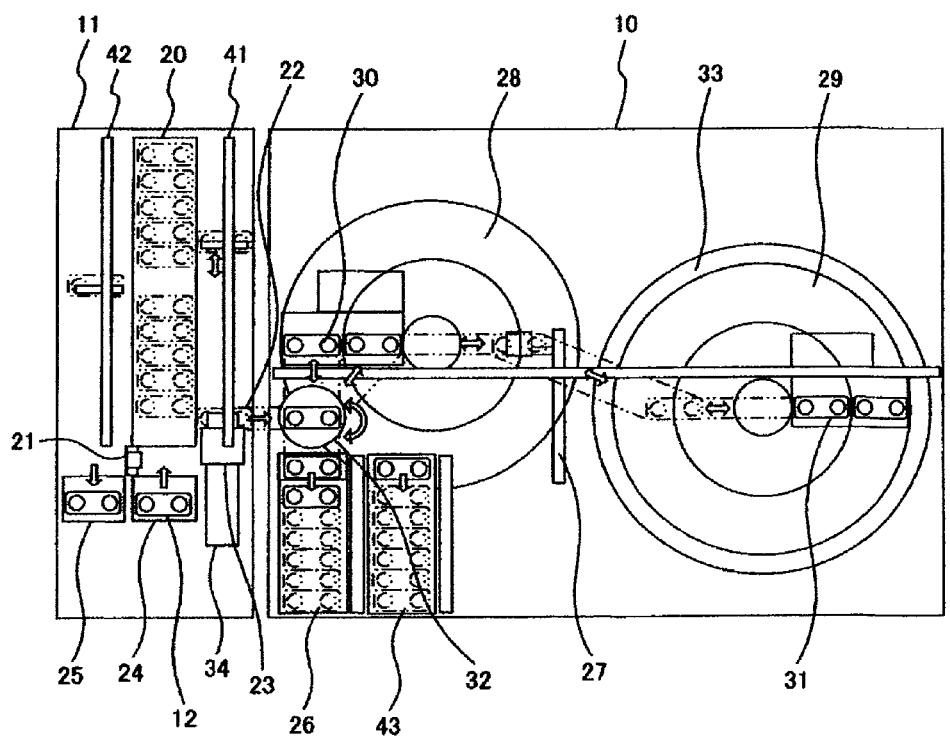
FIG. 2 is an illustration showing an outline of an automatic analyzer according to a second embodiment of the present invention.

The reagent replenishing unit 11 of the second embodiment shown in FIG. 2 includes replenishing reagent cassette supplementary loading means 24, a replenishing reagent cassette storage 20, a reagent cassette discharging mechanism 25, reagent cassette ejecting means 42, a reagent information reading mechanism 21, a reagent cassette unloading mechanism 41, a cap plug opening mechanism 23, a reagent cassette feeding mechanism 22 that feeds a reagent cassette from which a cap plug has been removed to a reagent cassette rotating mechanism 32 on the side of the analyzing unit 10, and a discarding section 34. The abovementioned reagent cassette transfer means includes the reagent cassette unloading mechanism 41 and the reagent cassette feeding mechanism 22.

The cap plug opening mechanism 23 is disposed at a position at which a cap plug opening position at which a cap plug is removed is located. The cap plug opening position serves also as a position from which a reagent cassette from which a cap plug has been removed is fed out onto the reagent cassette rotating mechanism 32.

When the operator loads a reagent cassette for replenishing into a loading port (not shown) of the replenishing reagent cassette supplementary loading means 24, the replenishing reagent cassette supplementary loading means 24 conveys the reagent cassette to a predetermined position. The reagent information reading mechanism 21 reads tag information on the reagent cassette conveyed onto the predetermined position. The tag information is determined by supply enable/disable determining means 21 in the same manner as in the first embodiment. If it is determined that the reagent cassette cannot be used for analysis in terms of, for example, the validity date and the amount of reagent still available for use, the reagent cassette is not fed to the replenishing reagent cassette storage 20; instead, the reagent cassette is transferred to the reagent cassette discharging mechanism 25 by the reagent cassette ejecting means 42 and discharged.

If the supply enable/disable determining means 21 determines that the reagent cassette 12 is usable for analysis, the reagent cassette 12 is transferred from the predetermined position to the replenishing reagent cassette storage 20 by the replenishing reagent cassette supplementary loading means 24.

A reagent cassette 12 for dispensing located at the replenishing reagent cassette storage 20 may temporarily need to be stored in another reagent storage. The operator intentionally issues a command to meet such a need from, for example, an operating screen. On receipt of the command, the reagent cassette ejecting means 42 fetches the corresponding reagent cassette in the replenishing reagent cassette storage 20 and transports the same to the reagent cassette discharging mechanism 25 for discharge.

When a reagent replenishing request (reagent replacement request) is received for a reagent cassette 12 for replenishing located at the replenishing reagent cassette storage 20, the corresponding reagent cassette is conveyed by the reagent cassette unloading mechanism 41 and placed at the cap plug opening position. The cap plug opening means 23 then removes the cap plug from the reagent cassette. The removed cap plug is discarded in the discarding section 34.

The reagent cassette from which the cap plug has been removed is fed from the cap plug opening position to the reagent cassette rotating mechanism 32 on the side of the analyzing unit 10. The second reagent cassette transfer mechanism of the reagent cassette transfer means conveys the reagent cassette to the dispensing reagent cassette storage (A) 28 or the dispensing reagent cassette storage (B) 29 for which the reagent replacement request was issued.

The second reagent cassette transfer mechanism of the reagent cassette transfer means also transports reagent cassettes for purposes other than replenishing. A reagent cassette that has a small amount of reagent available for use and that is to be replaced is unloaded from the dispensing reagent cassette storage (A) 28 or the dispensing reagent cassette storage (B) 29 to the discarding reagent cassette storage 26. The unloaded reagent cassette is left in the discarding reagent cassette storage 26 until the operator removes the same therefrom.

Figure 3:
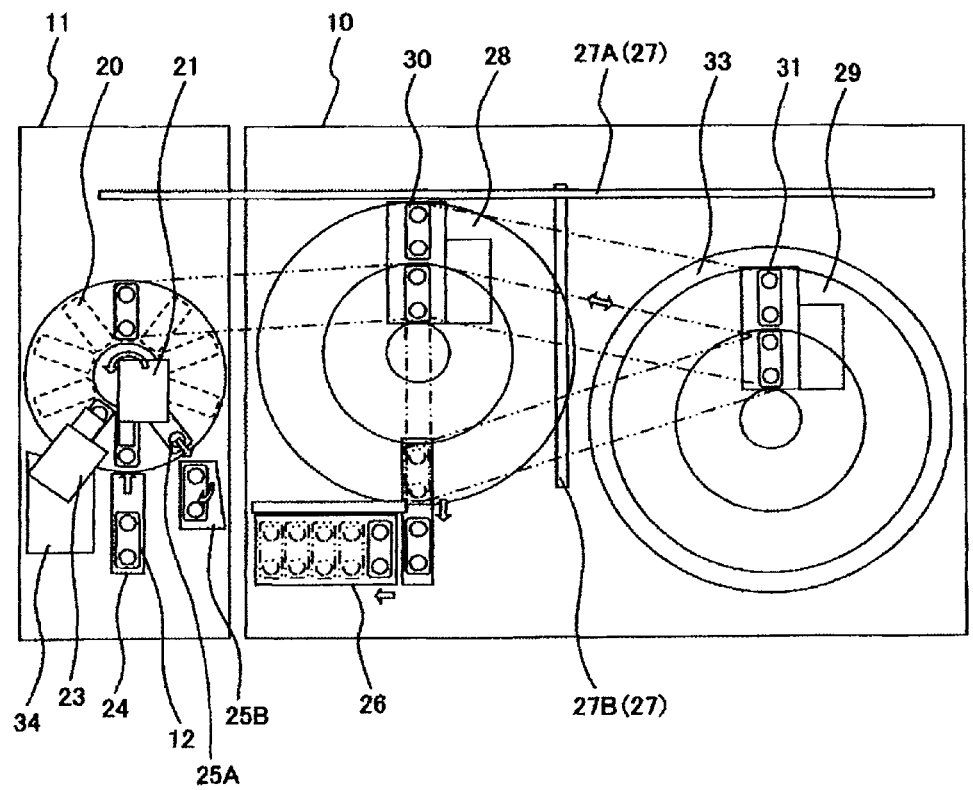
FIG. 3 is an illustration showing an outline of an automatic analyzer according to a third embodiment of the present invention.

A third embodiment will be described in detail below with reference to FIG. 3.

The third embodiment will be described with particular emphasis on differences from the first embodiment and descriptions of similarities which are denoted similar reference numerals will be omitted.

An automatic analyzer includes an analyzing unit 10, a reagent replenishing unit 11, and reagent cassette transfer means. The third embodiment differs from the first embodiment in the reagent cassette transfer means. The third embodiment is otherwise substantially similar to the first embodiment and the reagent cassette transfer means will be described below.

A reagent cassette transfer means 27 includes transport guide rails 27A, 27B. The transport guide rail 27A has a length extending from the reagent replenishing unit 11 to the analyzing unit 10. As a result, the reagent cassette transfer means 27 has a crosswise transfer range extending from a replenishing reagent cassette storage 20 included in the reagent replenishing unit 11 to a dispensing reagent cassette storage (B) 29 disposed on the right-hand side (on the side away from the reagent replenishing unit 11) of the analyzing unit 10.

The transport guide rail 27B disposed so as to cross the transport guide rail 27A extends in a longitudinal direction of the analyzing unit 10. The transport guide rail 27B has a length extending substantially an outside diameter of a dispensing reagent cassette storage (A) 28 included in the analyzing unit 10.

The reagent cassette transfer means 27 that includes, as described above, the transport guide rails 27A, 27B that cross each other forms a single reagent cassette transfer mechanism capable of transporting reagent cassettes over an extended range from the dispensing reagent cassette storage (A) 28 and the dispensing reagent cassette storage (B) 29 of the analyzing unit 10 to the replenishing reagent cassette storage 20 of the reagent replenishing unit 11.

The reagent cassette transfer means included in the first embodiment described earlier is formed from three transfer mechanisms including the first reagent cassette transfer mechanism on the side of the reagent replenishing unit, the second reagent cassette transfer mechanism on the side of the reagent replenishing unit, and the reagent cassette transfer relay section on the side of the reagent replenishing unit.

The reagent cassette transfer means of the third embodiment is formed from a single reagent cassette transfer mechanism and thus simple and easy to form as compared with the reagent cassette transfer means of the first embodiment. The reagent cassette transfer means formed from the three transfer mechanisms involves relay of reagent cassettes by way of the reagent cassette transfer relay section. However, the reagent cassette transfer means of the third embodiment is formed from the single reagent cassette transfer mechanism, which eliminates the need for relaying to thereby achieve efficient transport.

Other embodiments will be schematically described without referring to any drawings.

Some analysis may require a reagent that is not contained in any reagent cassette for dispensing located at the dispensing reagent cassette storage. Such a requirement is met as follows. Specifically, the reagent compatible with the inspection item of a specimen to be analyzed is identified and the reagent cassette transfer means unloads and transfers from the replenishing reagent cassette storage to the dispensing reagent cassette storage the specific reagent cassette for replenishing containing that particular reagent.

The replenishing reagent cassette stored in the replenishing reagent cassette storage is kept with the cap plug left fitted, so that the reagent cassette is stored longer than in the dispensing reagent cassette storage. Equipping the replenishing reagent cassette storage with a refrigerating function allows the reagent in the reagent cassette for replenishing to be maintained in a good condition.

Before being transferred to the dispensing reagent cassette storage, the cap plug is removed from the replenishing reagent cassette on the reagent replenishing unit side on which the replenishing reagent cassette storage is disposed. The cap plug opening means may be disposed at the reagent cassette transfer means included in the second and third embodiments, which simplifies arrangements of the reagent replenishing unit.

Reading means for reading the tag information attached to the reagent cassette may be disposed at the reagent cassette transfer means, which simplifies arrangements of the reagent replenishing unit.

DESCRIPTION OF REFERENCE NUMERALS

10: Analyzing unit
11: Reagent replenishing unit
12: Reagent cassette
20: Replenishing reagent cassette storage
21: Reading means
22: First reagent cassette transfer mechanism
23: Cap plug opening means
24: Replenishing reagent cassette supplementary loading means
25A: Reagent cassette ejecting means
26: Discarding reagent cassette storage
27: Reagent cassette transfer means
28: Dispensing reagent cassette storage (A)
29: Dispensing reagent cassette storage (B)
30: Reagent cassette loading port (A)
31: Reagent cassette loading port (B)
32: Reagent cassette rotating mechanism
33: Analyzing mechanism
34: Discarding section
41: Reagent cassette unloading mechanism
42: Reagent cassette ejecting means
43: Reagent cassette discharge storage

The invention claimed is:

1. An automatic analyzer comprising:
   an analyzing unit including: an analyzing mechanism; and a dispensing reagent cassette storage for storing reagent cassettes for dispensing;
   a reagent replenishing unit including a replenishing reagent cassette storage for storing in advance reagent cassettes for replenishing to be supplied as the reagent cassettes for dispensing, respectively;
   means for transferring a reagent cassette for replenishing which transfers a first reagent cassette that is judged to be used as a reagent cassette for dispensing to the dispensing reagent cassette storage from the replenishing reagent cassette storage;
   a reagent cassette ejecting mechanism which ejects, from the replenishing reagent cassette storage, a second reagent cassette for replenishing that is judged not to be used as a reagent cassette for dispensing, the reagent cassette ejecting mechanism being included in the reagent replenishing unit;
   a reagent information reading mechanism for reading reagent information included on the reagent cassette for replenishing; and
   a control computer configured to read the reagent information included on the reagent cassette for replenishing at a position of the replenishing reagent cassette storage via the reagent information reading mechanism one by one after the reagent cassette for replenishing is loaded in the replenishing reagent cassette storage, the control computer also configured to judge whether or not the reagent cassette for replenishing can be used for an analysis operation on the basis of the information read by the reagent information reading mechanism, wherein the reagent cassette ejecting mechanism ejects the second reagent cassette for replenishing which is judged not to be used by the control computer, where the second reagent cassette for replenishing, which is judged by the control computer not to be used, is not arranged continuously in the replenishing reagent cassette storage and is not transferred to the analyzing unit, and wherein at least one reagent cassette, which is not ejected by the reagent cassette ejecting mechanism and is arranged in the replenishing reagent cassette storage, is transferred to the dispensing reagent cassette storage from the replenishing reagent cassette storage through the means for transferring a reagent cassette in response to a reagent replenishing request from the control computer.

2. The automatic analyzer according to claim 1, wherein the reagent replenishing unit includes an ejected reagent cassette station at which the second cassette ejected by the reagent cassette ejecting mechanism is placed.

3. The automatic analyzer according to claim 1, wherein the reagent replenishing unit includes means for supplementary loading the reagent cassette for replenishing to be supplemented for the replenishing reagent cassette storage.

4. The automatic analyzer according to claim 1, wherein the reagent replenishing unit includes means for removing a cap plug from the reagent cassette for replenishing existing at the replenishing reagent cassette storage.

5. The automatic analyzer according to claim 4, wherein the reagent replenishing unit includes a discarding section at which the cap plug removed from the reagent cassette for replenishing is to be discarded.

6. The automatic analyzer according to claim 1, wherein the means for transferring a reagent cassette includes:

a reagent cassette transfer relay section disposed at the analyzing unit;

a first reagent cassette transfer mechanism disposed at the reagent replenishing unit, the first reagent cassette transfer mechanism for transferring the first reagent cassette for replenishing from the replenishing reagent cassette storage to the reagent cassette transfer relay section; and a second reagent cassette transfer mechanism disposed at the analyzing unit, the second reagent cassette transfer mechanism for transferring the first reagent cassette for replenishing from the reagent cassette transfer relay section to the dispensing reagent cassette storage.

7. The automatic analyzer according to claim 6, wherein the means for transferring a reagent cassette transfers the first reagent cassette to the dispensing reagent cassette storage based on a reagent replenishing request, and removes any reagent cassette for dispensing that is no longer necessary from the dispensing reagent cassette storage.

8. The automatic analyzer according to claim 6, wherein analysis requiring use of a reagent that is different from any reagent contained in any reagent cassette for dispensing existing at the dispensing reagent cassette storage, the means for transferring a reagent cassette unloads and transfers from the replenishing reagent cassette storage to the dispensing reagent cassette storage a specific reagent cassette for replenishing containing a reagent compatible with an inspection item of a specimen to be analyzed.

9. The automatic analyzer according to claim 1, wherein the replenishing reagent cassette storage has a refrigerating function.

10. The automatic analyzer according to claim 1, wherein the means for transferring a reagent cassette includes means for removing a cap plug from the reagent cassette for replenishing.

11. The automatic analyzer according to claim 1, wherein the means for transferring a reagent cassette includes means for reading, as the reagent information reading mechanism, reagent information on the reagent cassette for replenishing.

* * * * *